United States Patent [19]

Dombay et al.

[11] Patent Number: 4,621,080

[45] Date of Patent: Nov. 4, 1986

[54] SYNERGISTIC FUNGICIDAL COMPOSITIONS

[75] Inventors: Zsolt Dombay; Erzsébet Grega née Tóth; József Nagy, all of Miskolc; Csaba Pavliscsak, Sajóbábony; László Tasi; András Tóth, both of Miskolc; Oszkár Tóth, Debrecen; Judit Vitányi, Miskolc; Ferenc Bihari, Budapest; Péter Bohus, Budapest; Péter Inczédy, Budapest; István Magyari, Gödöllö; Marianna Kertész née Szabó, Budapest; László Wohl, Budapest; Attila Ferenczi, Budapest, all of Hungary

[73] Assignees: Eszakmagyarorszagi Vegyimuvek, Gyartelep; Budapesti Vegyimuvek, Budapest, both of Hungary

[21] Appl. No.: 625,945

[22] Filed: Jun. 29, 1984

[30] Foreign Application Priority Data

Jun. 30, 1983 [HU] Hungary ............................ 2366/83

[51] Int. Cl.$^4$ ..................... A01N 55/02; A01N 43/52
[52] U.S. Cl. ..................................... 514/187; 514/395
[58] Field of Search ................................ 514/187, 395

[56] References Cited

U.S. PATENT DOCUMENTS 4,086,339  4/1978  Matolcsy et al. .................. 514/187

OTHER PUBLICATIONS

The Merck Index, 10th Ed., No. 1771 (1983).

Primary Examiner—Jerome D. Goldberg
Assistant Examiner—F. Abramson
Attorney, Agent, or Firm—Karl F. Ross; Herbert Dubno

[57] ABSTRACT

The invention relates to a synergistic fungicidal composition containing more active ingredients comprising benzimidazole-2-ylmethylcarbamate and the zinc and manganese complexes of (8-oxyquinolinate)-(dimethyl dithiocarbamate) as active ingredients, optionally solid and/or liquid carrier(s) and other excipient(s).

The composition is of value especially in the treatment of infections caused by ustilaginales, powdery mildew and fusarium species on cereals.

9 Claims, No Drawings

SYNERGISTIC FUNGICIDAL COMPOSITIONS

FIELD OF THE INVENTION

The invention relates to synergistic fungicidal compositions comprising several active ingredients used in the treatment of fungal diseases of cereals, especially infections caused by ustilaginales, powdery mildew and fusarium species. The invention also resides in a method for combatting or preventing fungal infections by applying the said composition to the locus of the infection.

BACKGROUND OF THE INVENTION

It is well known from the art, that the most important pathogenic fungi of cereals (e.g. wheat, barley) are as follows:

smut diseases, such as bunt smut of wheat (*Tilletia foetida*), loose smut of barley (*Ustilago nuda*) and the fusarium species (Fusarium spp.) which infect the plant in embryomic stage partly in the soil, partly internally in the seed;

powdery mildew species (e.g. *Erypsiphe graminis*) which attack the plant in several stages of growth;

cereal fusarium fungi (*Fusarium graminearum*) and rusts (e.g. *Puccinia glumarum*) which attack the corn after earing.

The infections of the plant seed are treated by seed-dressing, while the later fungal attacks are treated with foliar spray application of different kinds of fungicides.

So far mercury containing compounds have been used for seed-dressing of corn. However, these compounds have several disadvantages. The health-detrimental and accumulating effect of mercury containing compounds is well known and the compounds do not protect the seeds from internal infections.

The activity of benzimidazol-2-ylmethylcarbamate (BMC, trade name: carbendazime) against phytopathogenic fungi was first described by H. Hampel and F. Löcher [Proc. Br. Insectic. Fungic. Conf. 7th, (1973) pp 127, 301], and the utility of this compound as an antifungal foliar spray was referred to in U.S. Pat. No. 3,657,443.

Powel reported on the protective fungicidal effect of the copper complex of 8-oxyquinoline the first time in the second half of the 1940's [Phytopathology, 36, p. 573, (1946)].

In Hungarian patent specification No. 171,736 the very favorable fungicidal effect of the mixed liganded (8-oxyquinolinate)-(dimethyl dithiocarbamate) metal complexes is described. These metal complexes are always more effective—especially if the central atom is zinc, manganese, copper, magnesium, iron, cadmium etc.—than the metal complexes of either 8-oxyquinolinate or dimethyl dithiocarbamate comprising the same ligand. It is further reported, that a mixture containing 1 part by weight of zinc complex and 1 part by weight of manganese complex is preferred.

According to Polish patent specification No. 104,686 a mixture of the copper complex of (8-oxyquinolinate)-(dimethyl dithiocarbamate) and carbendazime of a weight ratio 1:1 possesses synergistic effect against the fungi *Rhizoctonia solani, Phome betae* and *Helminthosporium gramineum*.

SUMMARY OF THE INVENTION

The compostion according to the invention contains benzimidazol-2-ylmethylcarbamate and zinc and manganese complexes of (8-oxyquinolinate)-(dimethyl dithiobarbamate) as active ingredients in a weight ratio of 1:3 to 2:1 and the weight ratio of the two different metal complexes of (8-oxyquinolinate)-(dimethyl dithiocarbamate) is 1:1.

The composition preferably contains 5% to 90% by weight of active ingredients, as well as solid or liquid carriers and other excipients.

According to a second aspect of the invention, there is provided a method of treating fungal infections of plants which comprises applying to said plants a fungicidally effective amount of a fungicidal formulation as defined above.

DETAILED DESCRIPTION OF THE INVENTION

The combinations of active ingredients defined in the above formulation are novel and have been found to be surprisingly effective in controlling or combatting fungal infections of cereals.

The composition exhibits synergistic effect in the range of a weight ratio of carbendazime and the metal complexes being 1:3 to 2:1. The preferred weight ratio of the two metal complexes is 1:1.

In the method of treating fungal infections the formulation can be applied by foliar application or it can be used as seed-dressing depending on the fungal attack to be treated. The amount and frequency of application is determined by the severity or expected severity of the fungal disease and, as is well known to those skilled in the art, by the age and condition of the crop.

In order to simplify manufacture, storage and transport, the combinations of the active ingredients are normally produced in a concentrate or powder form intended for dilution in a solvent to the degree necessary to enable the above mentioned application rates to be easily achieved. Such formulations are usually in the form of a wettable powder or dust, aqueous suspension, emulsifiable concentrate and granules. The concentrate formulations are intended for appropriate dilution prior to use. This formation of a dispersion can be carried out in conventional spray tanks suitable for the purpose.

Wettable powders or dusts comprise an intimate mixture of the active ingredients, one or more inert carriers and appropriate excipients. The inert carrier may be selected from the attapulgite clays, the montmorillonite clays, the diatomaceous earths, kaolins, micas, talcs and purified silicates.

Sufficient excipients may be found among the nonionic and ionic surfactants. E.g. sodium or calcium salts of polyacrylic acids and lignin sulphonic acid; the condensation of fatty acids or aliphatic amines or amides with ethylene oxyde and/or propylene oxide; fatty acid esters of glycerol, sorbitan, sucrose or pentaerythritol; condensates of these with ethylene oxide and/or propylene oxide; condensation products of fatty alcohols or alkyl phenols with ethylene oxide and/or propylene oxide; sulphates or sulphonates of these condensation products; alkali or alkaline earth metals of sulphuric or sulphonic acid esters; sodium alkylaryl sulphonates; polymers of ethylene oxide and copolymers of ethylene oxide and propylene oxide.

The composition according to the invention can be used most preferably in the form of an aqueous dispersion which active ingredient concentration depends on the manner of application, i.e. foliar application or seed-dressing.

SPECIFIC EXAMPLES

The invention is illustrated by the following, non-limiting examples.

Example 1

A seed-dressing suspension concentrate containing a film forming polymer is prepared with a total active ingredient concentration of 300 g/1000 ml by admixing the components given in Table 1. The solution containing solid particles is wet-milled until the diameter of the solid particles is less than 4 micron.

The combination can preferably be used for wet seed-dressing.

TABLE 1

| Compound | Amount of the compound added to the composition (g) | | | | |
|---|---|---|---|---|---|
| Carbendazime | 75 | 100 | 150 | 200 | 225 |
| (8-oxyquinolinate)-(dimethyl dithiocarbamate) Zn complex | 112.5 | 100 | 75 | 50 | 37.5 |
| (8-oxyquinolinate)-(dimethyl dithiocarbamate) Mn complex | 112.5 | 100 | 75 | 50 | 37.5 |
| ethyleneglycol | 90 | 90 | 90 | 90 | 90 |
| Ultrazine NA | 50 | 50 | 50 | 50 | 50 |
| Hoe S 1494 | 12 | 15 | 15 | 15 | 17.5 |
| Pluriol PE 10 500 | 18 | 15 | 15 | 15 | 12.5 |
| Morwith DM 21 | 200 | 200 | 200 | 200 | 200 |
| Rhodamin 2BU Flu | 5 | 5 | 5 | 5 | 5 | ion exchanged water completed to 1000 ml.

Example 2

A formulation containing a total 400 g/1000 ml of active ingredients is prepared. The combination of the composition is shown by Table 2. After the compounds are charged, the composition is filled with ion exchanged water to 1000 ml. and wet-milled until the particle size in the suspension achieves the size not higher than 5 micron.

The formulation is applied by foliar spray application after earing of corn.

TABLE 2

| Compounds | Charged amounts of the compounds (g) | | | | |
|---|---|---|---|---|---|
| Carbendazime | 100 | 133.4 | 200 | 266.8 | 300 |
| (8-oxyquinolinate)-(dimethyl dithiocarbamate) Zn complex | 150 | 133.3 | 100 | 66.6 | 50 |
| (8-oxyquinolinate)-(dimethyl dithiocarbamate) Mn complex | 150 | 133.3 | 100 | 66.6 | 50 |
| ethyleneglycol | 80 | 80 | 80 | 80 | 80 |
| Tensiofix XN6 | 30 | 30 | 30 | 30 | 30 |
| B 7425 | 15 | 15 | 10 | 5 | 5 |
| GG 21 | 15 | 15 | 20 | 25 | 25 |
| Rhodopol 23 | 0.1 | 0.1 | 0.1 | 0.1 | 0.1 |
| Ultrasil VN 3 | 0.1 | 0.1 | 0.1 | 0.1 | 0.2 |

Example 3

Wettable powder of 90% by weight of total active ingredients is prepared. The compounds are charged in an amount shown by Table 3, the composition is mixed, homogenized and milled until the size of the particles is 4 micron.

TABLE 3

| Compounds | Charged amounts of the compounds (g) | | | |
|---|---|---|---|---|
| Carbendazime | 22.5 | 36 | 45 | 60 |
| a 1:1 mixture of Zn and Mn complexes of (8-oxyquinolinate)-(dimethyl dithiocarbamate) | 67.5 | 54 | 45 | 30 |
| Netzer IS | 1.5 | 1.5 | 1.5 | 1.5 |
| Borresperse 3A | 3.5 | 3.5 | 3.5 | 3.5 |
| Zeolex 444 | 5 | 5 | 5 | 5 |

Example 4

Wettable powder suitable for use in foliar application as well as seed-dressing were prepared. The amounts of the compounds charged are listed in Table 4.

The concentration of the active ingredients in the compositions were 5, 10, 15 and 20% by weight. The substances were homogenized and milled as described in Example 3.

TABLE 4

| Compounds | Amounts of the compounds charged (g) | | | | |
|---|---|---|---|---|---|
| Carbendazime | 3 | 1.5 | 5 | 5 | 15 |
| a 1:1 mixture of Zn and Mn complexes of (8-oxyquinolinate)-(dimethyl dithiocarbamate) | 2 | 3.5 | 5 | 10 | 5 |
| Zeolex 444 | 15 | 15 | 10 | 15 | 10 |
| Silica earth | 72 | 72 | 72 | 62 | 62 |
| Netzer IS | 1.5 | 1.5 | 2 | 2 | 2 |
| Dispersing agent 1494 | 2.5 | 2.5 | 3 | 3 | 3 |
| Sulfit lye powder | 4 | 4 | 3 | 3 | 3 |

Example 5

This Example illustrates the typical synergistic activity observed when combinations of the invention are employed for control of fungal organisms.

NS-Róna 2 type winter wheat seeds infected with Fusarium spp. in 49.8 to 50.5% were infected with 0.2% by weight of *Tilletia foetida* spora calculated for the weight of the wheat.

The thus prepared seeds were seed-dressed with 2 l. of a combination containing 300 g/1000 ml. of active ingredients.

Further seed-dressing liquids were prepared containing only carbendazime or only zinc or manganese complexes of (8-oxyquinolinate)-(dimethyl-dithiocarbamate). The compositions were similarly prepared like in Example 1. As comparative formulation Dithane-M-45 was used in an amount of 600 g/t. This formulation contained 80% Mancoseb as active ingredient and is widely known and used.

A part of the infected seeds was not seed-dressed, it served as control in the experiments.

2×100 pieces of the treated and untreated seeds were incubated on Papavizas-type selective medium at 20° C. for 8 days and the Fusarium spp. infection was determined according to the developed sporulation and expressed in %.

Another part of the seeds was seeded on November 17 to plots of 2 m² prepared previously. 150 seeds were seeded to each line. 50 seeds were seeded into each plot and the plants emerged were counted on March 27. The extent of the *Tilletia foetida* infection was determined on July 2 in the period of complete maturity by counting the ears one by one.

The results obtained by randomized block design method in three replicates are listed in Table 5.

The results show, that the combinations exhibit synergistic activity in the range of a weight ratio of 1:3 to 2:1 of carbendazime and the metal complexes; they reduce the Fusarium spp. infection below 2%, while the Tilletia foetida infection is completely controlled.

The efficiency of the combinations against powdery mildew of crop was evaluated after the second spraying on 28th June. 100 productive plants selected by randomised method from each plots were examined, and the infection index was determined according to the following scale:

0 = symptom-free

TABLE 5

| Treatment | Dosage g/t | | | Rates of the active ingredients | Fusarium spp. infection % (laboratory) | Number of the plants emerged from 150 seeds | Number of the ears/plot | |
|---|---|---|---|---|---|---|---|---|
| | | | | | | | healthy | infected with Tilletia foetida |
| Carbendazime | 600 | — | — | — | 34.0 | 96.6 | 984.6 | 0.3 |
| (8-oxyquinolinate)-(dimethyl dithiocarbamate) Zn | | 600 | — | — | 29.0 | 105.3 | 1111.5 | 0.8 |
| (8-oxyquinolinate)-(dimethyl dithiocarbamate) Mn | | | 600 | — | 24.5 | 109.0 | 1154.4 | 0.5 |
| zinc and manganese complex | — | 150 | 450 | 1:3 | 19.0 | 116.2 | 1183.6 | 0.6 |
| zinc and manganese complex | — | 300 | 300 | 1:1 | 15.5 | 118.8 | 1196.5 | 0.4 |
| zinc and manganese complex | — | 450 | 150 | 3:1 | 21.2 | 112.3 | 1155.6 | 0.5 |
| Carbendazime + | 150 | 225 | 225 | 1:3 | 0 | 138.6 | 1403.2 | 0 |
| zinc and | 200 | 200 | 200 | 1:2 | 0 | 140.2 | 1452.4 | 0 |
| manganese | 300 | 150 | 150 | 1:1 | 0.5 | 129.8 | 1310.2 | 0 |
| complexes | 400 | 100 | 100 | 2:1 | 1.5 | 129.2 | 1302.5 | 0 |
| | 450 | 75 | 75 | 3:1 | 9.0 | 117.6 | 1196.6 | 0 |
| infected with ustilaginales Control | — | — | — | — | 50.5 | 84.7 | 859.7 | 92.7 |
| Non-infected cont. | — | — | — | — | 49.8 | 92.0 | 959.6 | 9.4 |
| Dithane M-45 (80% MANCOSEB) | 600 | | | | 48.3 | 100.0 | 972.3 | 6.1 |

Example 6

The test shows the protective activity of the combaintions on winter wheat against powdery mildew and earfusarium. The tested combinations were applied as foliar sprays in field tests.

NS-Róna 2 type wheat seeds were seeded on plots of 5 ha. on October 25th into the soil adequately prepared.

The well emerged plants saved from winterkill were weed controlled by a herbicide containing MCPA as active ingredient, generally used in cultivation of cereals by spraying by airoplane, thereafter a sulphur comprising formulation (Sulphur 900 FW) was applied as a foliar spray at the end of tillage (on 5th May) in order to supress the incipient powdery mildew infection.

Later the selected plots were treated the first time at the end of earing (on 26th May), the second time on 10th June by spraying by airplane. In the treatment carbendazime (BCM), Dithane M-45, zinc and manganese complexes of (8-oxyquinolinate)-(dimethyl dithiocarbamate) and the combination according to the invention were used in 400 FW formulation, described in Example 2. 50 l/ha. of water were used for spraying, the amount of the active ingredients applied was 0.25 to 1.0 kg/ha.

1 = the infection is 5% or less
2 = the infection is within the range of from 6% to 10%
3 = the infection is within the range of from 11% to 25%
4 = the infection is within the range of from 26% to 50%
5 = the infection is within the range of from 51% to 75%
6 = the infection is within the range of from 76% to 100%

The percent of the infection expresses the rate of the healthy and infected leaf surfaces or the average coverage of the leaf surface of the four leaf nodes by mycelium.

The infection index was calculated from the data obtained according to the following formula:

$$Fi = \frac{a_i \cdot f_i}{n}$$

wherein $a_i$ stands for the infection values according to the above scale, $f_i$ represents the frequency of a certain scale value, while n stands for the number of the plants examined.

The experimental results are listed in Table 6.

TABLE 6

| Treatment | Dosage kg/ha. | | | Rate of the active ingredients | Number of the infected plants belonging to each scale values | | | | | | | $F_1$ |
|---|---|---|---|---|---|---|---|---|---|---|---|---|
| | | | | | 0 | 1 | 2 | 3 | 4 | 5 | 6 | |
| Carbendazime | 0.25 | — | — | — | — | 64 | 260 | 76 | — | — | — | 2.03 |
| | 0.50 | — | — | — | — | 284 | 116 | — | — | — | — | 1.29 |
| | 1.00 | — | — | — | 16 | 272 | 112 | — | — | — | — | 1.24 |
| zinc complex | — | 1.0 | — | — | — | — | — | 320 | 200 | 152 | 18 | 4.38 |

TABLE 6-continued

| Treatment | Dosage kg/ha. | | | Rate of the active ingredients | Number of the infected plants belonging to each scale values | | | | | | | $F_1$ |
|---|---|---|---|---|---|---|---|---|---|---|---|---|
| | | | | | 0 | 1 | 2 | 3 | 4 | 5 | 6 | |
| | — | 2.0 | — | — | — | — | — | 72 | 200 | 84 | 44 | 4.25 |
| manganese | — | — | 1.0 | — | — | — | — | 88 | 184 | 72 | 56 | 4.24 |
| complex | — | — | 2.0 | — | — | — | — | 76 | 232 | 92 | — | 4.04 |
| the mixture of | — | 0.25 | 0.75 | 1:3 | — | — | — | 48 | 132 | 100 | — | 4.28 |
| the zinc and | — | 0.50 | 0.50 | 1:1 | — | — | 72 | 274 | 56 | — | — | 2.96 |
| manganese complexes | — | 0.75 | 0.25 | 3:1 | — | — | — | 88 | 180 | 112 | 20 | 4.16 |
| the composition according to the invention | 0.25 | 0.38 | 0.37 | 1:3 | 72 | 296 | 16 | 16 | — | — | — | 0.94 |
| | 0.33 | 0.34 | 0.33 | 1:2 | 76 | 292 | 32 | — | — | — | — | 0.89 |
| | 0.50 | 0.25 | 0.25 | 1:1 | 68 | 276 | 56 | — | — | — | — | 0.97 |
| | 0.67 | 0.16 | 0.16 | 2:1 | — | 332 | 68 | — | — | — | — | 1.17 |
| | 0.75 | 0.12 | 0.12 | 3:1 | — | 324 | 74 | — | — | — | — | 1.19 |
| untreated control | — | — | — | — | — | — | — | — | — | 160 | 240 | 5.60 |
| Dithane M-45 | 1.0 | | | | 10 | 183 | 115 | 92 | | | | 1.72 |

The test results very expressively show that the combinations containing carbendazime and metal complexes at the weight ratio of 1:3 to 1:1 can adequately prevent the powdery mildew infection even at a dose of 1 kg of active ingredients/ha. and exhibit a synergistic effect in these ratios of the active ingredients. The results also show, that they are more effective than the well known and widely used Dithane M-45.

In the course of the examinations of Fusarium spp. infections 500 ears were infected with Fusarium spp. on each plot and after harvesting the yield by combine-harvester on 16th July, 500 seed samples were taken from each plot.

The Fusarium spp. infection of these seeds was examined by microscopic test after incubating them on Papavizas-type medium at 20° C. for 8 days. When the total infection was measured, the seeds were incubated without any surface disinfection, while in order to determine the internal infection of the seeds, the seeds were previously soaked in 1% Neomagnol solution for ten minutes then washed with sterile water on the surface.

The test results are listed in Table 7.

activity even when a dose of 1 kg. of active ingredients/ha. is used for the treatment, and assure a significant protection against the infection of the ears as well as the internal and external infection of the seed. Comparing with Dithane M-45 which is well known and widely used in agriculture, it is also demonstrated that the combinations according to the invention are more effective.

Example 7

Spring barley was treated against powdery mildew, helminto-sporium and smut infection according to Example 6. The combinations described in Example 4, and an 1:1 mixture of the widely known Agrocit (comprising 50% of Benomyl) and Dithane M-45 (comprising 80% of Mancoseb) were used for powdering the stand. The infection indexes were calculated according to Example 6. The results are summarized in Table 8.

TABLE 8

| Treatment | Dosage kg/ha. | Rate of the active ingredients | Infection index | | us-tilagi-nales |
|---|---|---|---|---|---|
| | | | mildew | helminto sporium | |
| Carbendazime | 2.0 | | 1.98 | 0.33 | 3.30 |

TABLE 7

| Treatment | Dosage kg/ha. | | | Rate of the active ingredients | Rate of the ear infection with Fusarium spp. (%) | Rate of the seed infection with Fusarium spp. (%) | |
|---|---|---|---|---|---|---|---|
| | | | | | | total | internal |
| Carbendazime | 0.25 | — | — | — | 8.5 | 15.45 | 13.58 |
| | 0.50 | — | — | — | 6.5 | 11.95 | 10.16 |
| | 1.00 | — | — | — | 5.25 | 11.05 | 9.34 |
| zinc complex | — | 1.00 | — | — | 6.5 | 10.52 | 9.54 |
| | — | 2.00 | — | — | 5.5 | 9.24 | 8.33 |
| manganese complex | — | — | 1.00 | — | 6.4 | 11.68 | 10.06 |
| | — | — | 2.00 | — | 5.5 | 10.53 | 9.31 |
| a mixture of zinc and manganese complex | — | 0.25 | 0.75 | 1:3 | 5.5 | 10.78 | 9.96 |
| | — | 0.50 | 0.50 | 1:1 | 5.25 | 10.25 | 9.50 |
| | — | 0.75 | 0.25 | 3:1 | 5.5 | 11.05 | 9.84 |
| the composition according to the invention | 0.25 | 0.38 | 0.37 | 1:3 | 0.50 | 5.50 | 4.40 |
| | 0.33 | 0.34 | 0.33 | 1:2 | 0.65 | 5.84 | 4.58 |
| | 0.50 | 0.25 | 0.25 | 1:1 | 2.50 | 7.36 | 6.25 |
| | 0.67 | 0.16 | 0.17 | 2:1 | 2.75 | 7.73 | 6.43 |
| | 0.75 | 0.125 | 0.125 | 3:1 | 3.25 | 7.90 | 6.67 |
| control | — | — | — | — | 11.50 | 38.78 | 31.25 |
| Dithane M-45 | 1.0 | — | — | — | 6.3 | 16.25 | 13.82 |

The experimental results expressively show, that the combinations containing carbendazime and metal complexes in a weight ratio of 1:3 to 1:2 exhibit a synergistic TABLE 8-continued

| | Rate of the | Infection index | us- | and *Tilletia foetida* infection. Their antifungal effect is significantly higher than that of Quinolate V-4X widely used as fungicide.

TABLE 9

| Treatment | Dosage g/t | | | Rate of the active ingredients | Infection with Fusarium spp. (%) | Infection with Aspergilus (%) | Infection with Penicillium (%) | Number of the plants emerged from 150 seeds | Number of the ears per plots | |
|---|---|---|---|---|---|---|---|---|---|---|
| | | | | | | | | | healthy | infected with *Tilletia foetida* |
| Carbendazime | 1800 | — | — | — | 35.3 | 21.4 | 18.3 | 96.8 | 983.7 | 0.5 |
| (8-oxyquinolinate)-(dimethyl dithiocarbamate) Zn complex | — | 1800 | — | — | 27.1 | 17.3 | 15.2 | 103.4 | 1078.4 | 0.7 |
| (8-oxyquinolinate)-(dimethyl dithiocarbamate) Mn complex | — | — | 1800 | — | 23.2 | 12.9 | 10.3 | 108.1 | 1125.3 | 0.4 |
| the mixture of | — | 450 | 1350 | 1:3 | 18.7 | 9.3 | 8.1 | 118.7 | 1192.7 | 0.7 |
| the zinc and | — | 900 | 900 | 1:1 | 13.0 | 7.5 | 6.5 | 120.3 | 1305.8 | 0.5 |
| manganese complexes | — | 1200 | 600 | 2:1 | 17.4 | 8.2 | 8.7 | 116.5 | 1181.9 | 0.3 |
| Carbendazime + | 450 | 675 | 675 | 1:3 | 0 | 0 | 0 | 145.2 | 1496.0 | 0 |
| zinc and | 720 | 540 | 540 | 1:1.5 | 0.98 | 0 | 0 | 143.1 | 1494.2 | 0 |
| manganese | 900 | 450 | 450 | 1:1 | 1.02 | 0.4 | 0 | 138.0 | 1491.3 | 0 |
| complex | 1200 | 300 | 300 | 2:1 | 1.43 | 0.84 | 0 | 123.8 | 1300.4 | 0 |
| untreated control | — | — | — | — | 50.3 | 40.5 | 32.4 | 86.0 | 873.8 | 10.8 |
| Quinolate V-4X | 2000 | — | — | — | 8.0 | 14.4 | 6.0 | 94.0 | 975.0 | 2.5 |

| Treatment | Dosage kg/ha. | active ingredients | mildew | helmintosporium | tilaginales |
|---|---|---|---|---|---|
| zinc complex | 2.0 | | 4.12 | 0.60 | 4.08 |
| manganese complex | 2.0 | | 4.00 | 0.56 | 3.97 |
| a mixture of | 2.0 | 1:3 | 4.06 | 0.57 | 4.53 |
| the zinc and | 2.0 | 1:1 | 3.14 | 0.48 | 4.21 |
| manganese complexes | 2.0 | 3:1 | 3.96 | 0.52 | 4.68 |
| composition | 2.0 | 1:2 | 0.95 | 0.00 | 1.84 |
| according to | 2.0 | 3:1 | 1.20 | 0.00 | 2.05 |
| the invention | 2.0 | 1:1 | 1.00 | 0.00 | 1.98 |
| | 2.0 | 1.5:1 | 1.04 | 0.00 | 2.00 |
| untreated control | — | — | 5.80 | 0.70 | 5.30 |
| Agrocit + Dithane M-45 | 1.0 + 1,0 | — | 2.06 | 0.36 | 2.60 |

The data listed in Table 8 show very expressively, that the combinations according to the invention containing carbendazime and metal complexes in the weight ratio of 3:1 to 1:1, wherein the weight ratio of the zinc and manganese complexes is 1:1, give a sufficient protection against all the three kinds of fungal diseases, and the combinations exhibit a synergistic effect in these ratios of the active ingredients. The antifungal effect of the combinations according of the invention is significantly higher than the combination of Agrocit and Dithane M-45 applied in the same dose.

Example 8

Winder barley was seed-dressed against the infection of Fusarium spp., Aspergilus, Penicillium and *Tilletia foetida*. The experiments were carried out similarly to Example 5, the combinations described in Example 3 were used and Quinolate V-4X (15% of oxyquinolate copper complex+50% of carboxine) well known in the art was applied as control.

The experimental results are listed in Table 9.

The test results show, that the combinations according to the invention in the weight ratio of 1:3 to 2:1 of the active ingredients exhibit synergistic activity, they suppress the Fusarium spp. and Aspergilus infection below 2%, while completely control the Penicillium

We claim:

1. A synergistic fungicidal composition for the treatment of Fusarium spp., Aspergillus, Penicillium, or *Tilletia foetida*, which comprises:
    (a) benzimidazole-2-yl-methyl carbamate;
    (b) zinc 8-oxyquinolinate-dimethyl-dithiocarbamate complex; and
    (c) manganese 8-oxyquinolinate-dimethyl-dithiocarbamate complex;
wherein the weight ratio of the benzimidazole-2-yl-methyl carbamate to the combined zinc and manganese 8-oxyquinolinate-dimethyl-dithiocarbamate complexes is 1:3 to 2:1 and the weight ratio between the zinc 8-oxyquinolinate-dimethyl-dithiocarbamate complex and the manganese 8-oxyquinolinate-dimethyl-dithiocarbamate complex is 1:1, as active ingredients.

2. A method of combatting Fusarium spp. or *Tilletia foetida* in winter wheat, which comprises the step of applying a fungicidally effective amount of the composition as defined in claim 1 to said fungus.

3. A method of combatting Fusarium spp. Aspergillus, Penicillum or *Tilletia foetida* in winter barley, which comprises the step of applying a fungicidally effective amount of the composition defined in claim 1 to said fungus.

4. A synergistic fungicidal composition for the treatment of Fusarium spp., which comprises:
    (a) benzimidazole-2-yl-methyl carbamate;
    (b) zinc 8-oxyquinolinate-dimethyl-dithiocarbamate complex; and
    (c) manganese 8-oxyquinolinate-dimethyl-dithiocarbamate complex;
wherein the weight ratio of the benzimidazole-2-yl-methyl carbamate to the combined zinc and manganese 8-oxyquinolinate-dimethyl-dithiocarbamate complexes is 1:3 to 1:2 and the weight ratio between the zinc 8-oxyquinolinate-dimethyl-dithiocarbamate complex and the manganese 8-oxyquinolinate-dimethyl-dithiocarbamate complex is 1:1, as active ingredients.

5. A method of combatting Fusarium spp. in corn, which comprises the step of applying a fungicidally effective amount of the composition as defined in claim 4 to said fungus.

6. A synergistic fungicidal composition for the treatment of powdery mildew, which comprises:
(a) benzimidazole-2-yl-methyl carbamate;
(b) zinc 8-oxyquinolinate-dimethyl-dithiocarbamate complex; and
(c) manganese 8-oxyquinolinate-dimethyl-dithiocarbamate complex;

wherein the weight ratio of the benzimidazole-2-yl-methyl carbamate to the combined zinc and manganese 8-oxyquinolinate-dimethyl-dithiocarbamate complexes is 1:3 to 1:1 and the weight ratio between the zinc 8-oxyquinolinate-dimethyl-dithiocarbamate complex and the manganese 8-oxyquinolinate-dimethyl-dithiocarbamate complex is 1:1, as active ingredients.

7. A method of combatting powdery mildew in winter wheat, which comprises the step of applying a fungicidally effective amount of the composition defined in claim 6 to said fungus.

8. A synergistic fungicidal composition for the treatment of powdery mildew, helminto sporium, or Ustilago nuda, which comprises:
(a) benzimidazole-2-yl-methyl carbamate;
(b) zinc 8-oxyquinolinate-dimethyl-dithiocarbamate complex; and
(c) manganese 8-oxyquinolinate-dimethyl-dithiocarbamate complex;

wherein the weight ratio of the benzimidazole-2-yl-methyl carbamate to the combined zinc and manganese 8-oxyquinolinate-dimethyl-dithiocarbamate complexes is 3:1 to 2:1 and the weight ratio between the zinc 8-oxyquinolinate-dimethyl-dithiocarbamate complex and the manganese 8-oxyquinolinate-dimethyl-dithiocarbamate complex is 1:1.

9. A method of combatting powdery mildew, helminto sporium, or *Ustilago nuda* in spring barley, which comprises the step of applying a fungicidally effective amount of the composition defined in claim 8 to said fungus.

* * * * *